US00PP35776P2

(12) United States Plant Patent
Olesen

(10) Patent No.: US PP35,776 P2
(45) Date of Patent: Apr. 30, 2024

(54) ROSE PLANT NAMED 'POULPAR131'

(50) Latin Name: *Rosa hybrida*
Varietal Denomination: Poulpar131

(71) Applicant: Mogens Nyegaard Olesen, Fredensborg (DK)

(72) Inventor: Mogens Nyegaard Olesen, Fredensborg (DK)

(73) Assignee: Poulsen Roser A/s, Fredensborg (DK)

( * ) Notice: Subject to any disclaimer, the term of this patent is extended or adjusted under 35 U.S.C. 154(b) by 0 days.

(21) Appl. No.: 18/445,479

(22) Filed: Sep. 8, 2023

(30) Foreign Application Priority Data

Sep. 30, 2022 (QZ) ..... PBR 2022/2173

(51) Int. Cl.
*A01H 5/02* (2018.01)
*A01H 6/74* (2018.01)

(52) U.S. Cl.
USPC ..... Plt./135

(58) Field of Classification Search
USPC ..... Plt./101, 130, 135
See application file for complete search history.

*Primary Examiner* — Susan McCormick Ewoldt

(57) ABSTRACT

A new rose plant of the Miniature class which has abundant, orange flowers and attractive foliage. This new and distinct variety has shown to be uniform and stable in the resulting generations from asexual propagation.

1 Drawing Sheet

Botanical designation: *Rosa hybrida.*

Variety denomination: 'Poulpar131'.

This application claims priority to Plant Breeder's Rights Application Number 2022/2173, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpar131', originated as a single seedling from the stated cross.

The new variety may be distinguished from its male pollen parent and female seed parent primarily by the following characteristics. The male pollen parent plant is a shrub rose growing to 100 cm tall and has pink flowers, while the claimed plant grows to 40 cm and has orange flowers. The female seed parent is a compact landscape rose with pink flowers while the claimed plant is a miniature hybrid tea rose with orange flowers.

The objective of the hybridization of this rose variety was to create a new and distinct variety with unique qualities, such as:

1. Uniform and abundant orange flowers with long lasting quality;
2. Vigorous, but compact growth when propagated on its own roots;
3. Exceptional disease resistance.

This combination of qualities is not present in previously available commercial cultivars of this type, known to the inventor, and distinguish 'Poulpar131' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpar131' was selected in the spring of 2015 by the inventor as a single plant from the progeny of the aforementioned hybridization.

Asexual reproduction of 'Poulpar131' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpar131' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar131'. Specifically illustrated in the drawing are petals detached revealing reproductive flower parts, partially open and fully open flower viewed from above, side view of flower bud and partially opened flower, bare stem exhibiting prickles, mature and juvenile leaves, and a cluster of flower buds on a branch. Plants shown are 4 months in age.

DETAILED DESCRIPTION OF THE VARIETY

The following is a description of 'Poulpar131', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpar109', U.S. Plant Pat. No. 30,349 are compared to the claimed plant. While 'Poulpar131' has 56 flower petals, 'Poulpar109' has 30 flower petals. The claimed plant has a flower diameter of 45 mm while 'Poulpar109' has a flower diameter of 55 mm. Open flowers of 'Poulpar131' are generally Orange-Red Group N32B in color while 'Poulpar109' has a general tonality of Orange Group 27C and Orange Group 29B, and Red Group 38A.

FLOWER AND FLOWER BUD

Blooming habit: Continuous.

Flower bud:

- *Size.*—Upon opening, 21 mm in length from base of receptacle to end of bud. Bud diameter is 10 mm.
- *Bud form.*—Ovoid.
- *Bud color.*—As sepals divide petals are Orange Red Group N30A.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—25 mm long, 6 mm wide.
- *Receptacle.*—Texture: Smooth. Size: 6 mm in height, 6 mm wide. Color: Yellow-Green Group 144A. Shape: Campanulate.
- *Pedicel.*—Surface: Smooth. Length: About 43 mm. Diameter: 2 mm on average. Color: Yellow-Green Group 144A. Strength: Strong.
- *Peduncle.*—Length: About 1.5 cm. Diameter: 2 mm. Color: Yellow-Green Group 145A. Texture: Smooth.

Flower bud development: Flower buds are borne in clusters of 3 to 5 flower buds per stem.

Flower bloom:

- *Fragrance.*—Light floral.
- *Duration.*—The blooms have a duration on the plant of approximately 28 days. Petals fall cleanly away from plant after flowers have fully matured.
- *Size.*—Flower diameter is 45 mm when open. Flower depth is about 16 mm.
- *Flower shape.*—Viewed from above, star shaped. General shape is a rosette with many slightly overlapping petals of different sizes.
- *Shape of flower, side view.*—The upper portion is flat. The lower portion is flat.

Petalage: Under normal conditions, flowers have about 56 petals.

General tonality of flower: Open flowers are Orange-Red Group N32B.

Petal color:

- *Upon opening, outer petals.*—Upper surface: Orange-Red Group 30A with a moderate sized basal petal spot Yellow Group 9B. Occasionally there are streaks of Yellow Group 8D. Lower surface: Red Group 41B at margins and the middle zone, splashed with Yellow Group 8A. Basal zone petal spot Yellow Group 8A moderate sized.
- *Upon opening, inner petals.*—Upper surface: Orange-Red Group N30A with intonations at the basal zone Yellow Group 9A. Lower surface: Red Group 40C and Red Group 45C blend. Basal zone Yellow Group 9B. Occasionally there are streaks of Yellow Group 9B.
- *After opening, outer petals.*—Upper surface: Orange-Red Group 32B with a moderate sized basal petal spot Yellow Group 9B. Lower surface: Red Group 40C with streaks of Yellow Group 8B. Petal spot Yellow Group 8B.

Petals:

- *Petal Reflex.*—Bilateral, strong, reflex.
- *Margin.*—Outer petals are entire and uniform. Inner petals have a cleft in the margin. No undulations.
- *Shape.*—Broad and elliptic. Apex shape: Rounded. Base shape: Acute.
- *Size.*—About 20 mm (l)×20 mm (w).
- *Texture.*—Smooth.
- *Thickness.*—Average.

Petaloids:

- *Size.*—About 12 mm (l) by 7 mm (w).
- *Quantity.*—About 15.
- *Shape.*—Elliptical with an acute base and rounded apex.
- *Color.*—On the upper surface Orange-Red Group N30A with a petaloid spot at the basal zone Yellow Group 9A. The lower surface is Red Group 45C with a petaloid spot at the base Yellow Group 9B.

Reproductive flower parts:

- *Pollen.*—None observed.
- *Anthers.*—Size: 1.5 mm in length. Color: Yellow Group 10B. Quantity: 34 on average.
- *Filaments.*—Color: Yellow-Orange Group 14B. Length: 3 mm.
- *Pistils.*—Length: 2 mm. Quantity: 31 on average.
- *Stigmas.*—Color: Yellow-White Group 158A.
- *Styles.*—Color: Red Group 45A.
- *Location of stigmas.*—Inferior in location relative to the length of the filaments and the height of the anthers.
- *Hips.*—None Observed.

PLANT

Plant growth: Upright and well branched. Plants are about 40 cm in height and 37 cm wide.

Stems:

- *Color of juvenile growth.*—Yellow-Green Group 144A.
- *Color of mature growth.*—Yellow-Green Group 144A.
- *Length.*—Canes are about 23 cm from the base of the plant to the flowering portion.
- *Diameter.*—About 4 mm.
- *Internodes.*—On mature canes about 25 mm between nodes.
- *Surface texture.*—Young wood: Smooth. Older wood: Smooth.

Long prickles:

- *Incidence.*—About 13 prickles per 10 cm of stem.
- *Size.*—Average length of prickles on mature stems is 6 mm.
- *Shape.*—Upper portion is linear. Lower portion is concave.
- *Color.*—Juvenile prickles: Yellow-Green Group 144C. Mature prickles: Yellow-Green Group 144C.

Plant foliage:

*Compound leaf.*—75 mm (l)×50 (w).

*Quantity.*—4 leaves per 10 cm of stem on average.

*Leaf bearing angle to the stem.*—45 degrees.

*Color of juvenile foliage.*—Upper side: Yellow-Green Group 144A. Marginal intonations of Greyed-Red Group 180A. Lower side: Yellow-Green Group 146D. Marginal intonations of Greyed-Red Group 180A.

*Color of mature foliage.*—Upper side: Yellow-Green Group 147A. Lower side: Yellow-Green Group 147B.

Plant leaves and leaflets:

*Stipules.*—Size: 10 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 25 mm. Diameter: 1.5 mm. Upper surface color: Yellow-Green Group 144A. Lower surface color: Yellow-Green Group 144A.

*Rachis.*—Length: 27 mm. Upper surface color: Yellow-Green Group 144A. Lower surface color: Yellow-Green Group 144A.

*Leaflet.*—Quantity: Normally 5 to 7 leaflets. Margins: Serrated. Size: Terminal leaflets are about 46 mm long, 24 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpar131' substantially as described and illustrated herein.

* * * * *

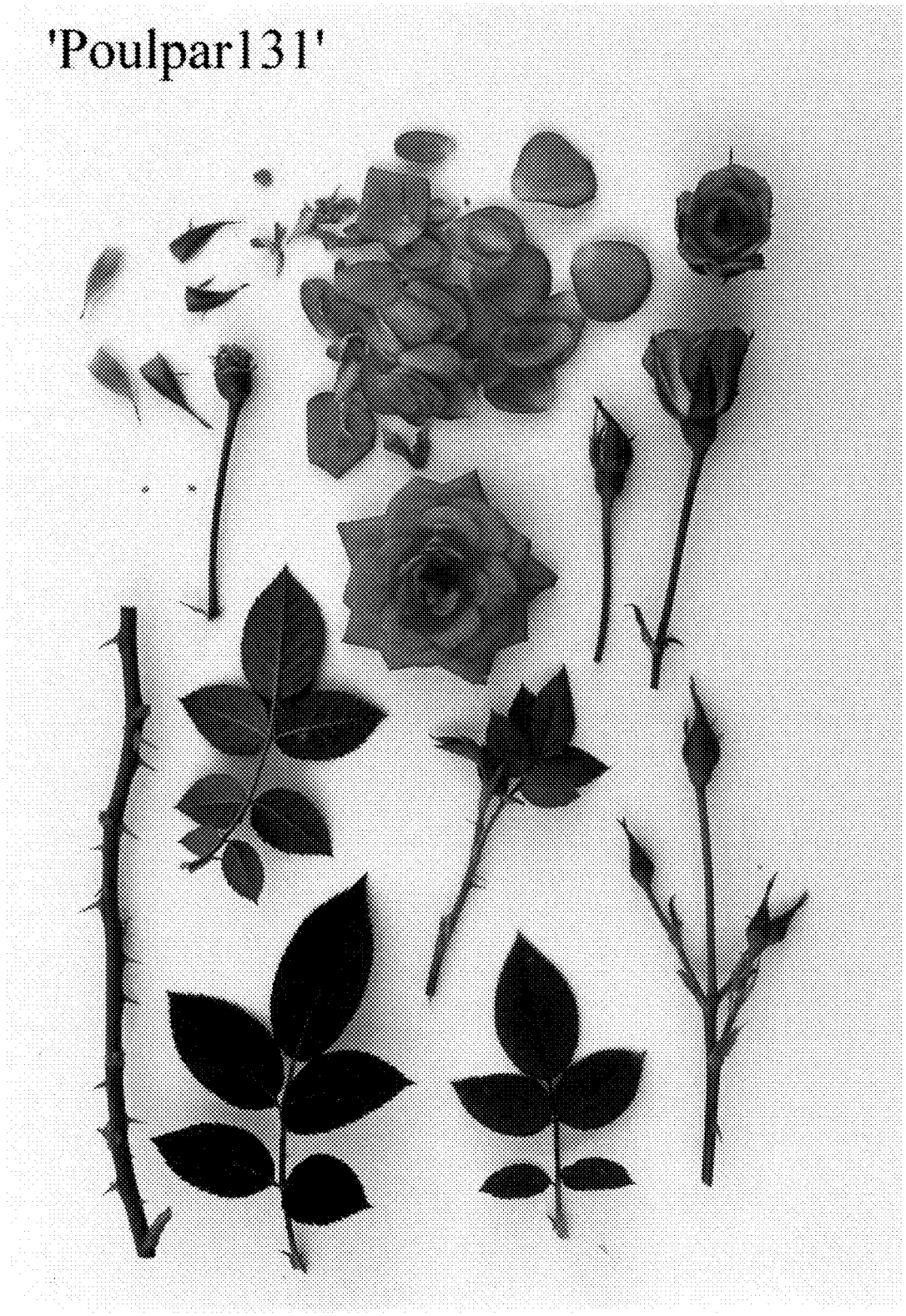
'Poulpar131'